United States Patent [19]

Riess et al.

[11] Patent Number: 5,573,757
[45] Date of Patent: Nov. 12, 1996

[54] VISCOELASTIC COMPOSITIONS CONTAINING CONCENTRATED FLUORINATED COMPOUNDS THEIR METHOD OF PREPARATION AND THEIR USES

[75] Inventors: Jean G. Riess, Falicon; Marie-Pierre Krafft, Nice, both of France

[73] Assignee: Alliance Pharmaceutical Corp., San Diego, Calif.

[21] Appl. No.: 316,731

[22] Filed: Oct. 3, 1994

[30] Foreign Application Priority Data

Oct. 4, 1993 [FR] France ................... 93 00786

[51] Int. Cl.⁶ .................... A61K 31/74; A61K 31/025
[52] U.S. Cl. .................... 424/78.02; 514/755; 514/756; 514/832; 514/743
[58] Field of Search .................... 424/78.02; 514/755, 514/756, 832; 174/743

[56] References Cited

U.S. PATENT DOCUMENTS 4,366,169  12/1982  White .
4,423,077  12/1983  Sloviter .
4,569,784   2/1986  Moore .
4,917,930   4/1990  McCormick .
5,073,378  12/1991  Shoshan et al. .
5,185,099   2/1993  Delpuech et al. .

FOREIGN PATENT DOCUMENTS 0158996  10/1985  European Pat. Off. .
2630347  10/1989  France .
9015807  12/1990  WIPO .
9301798   2/1993  WIPO .
9309762   5/1993  WIPO .
9309787   5/1993  WIPO .

*Primary Examiner*—Paul J. Killos
*Attorney, Agent, or Firm*—Knobbe, Martens Olson & Bear

[57] ABSTRACT

Compositions for topical application in gel form comprising a fluorocarbon or perfluorocarbon compound or mixtures thereof at a concentration of at least about 75% v/v, a minor quantity of a surface active agent and an aqueous phase.

The compositions provide a storage-stable high concentration fluorocarbon gel that is prepared without the use of thickeners or additional stabilizing agents. The gels are useful in formulations for pharmaceutical, cosmetic purposes and for other products as well.

45 Claims, No Drawings

VISCOELASTIC COMPOSITIONS CONTAINING CONCENTRATED FLUORINATED COMPOUNDS THEIR METHOD OF PREPARATION AND THEIR USES

This application claims priority to French application No. 93-00786, filed Oct. 4, 1993.

The present invention relates to viscoelastic compositions or gels, such as protective creams and lubricating agents, formulated for cosmetic, biology, therapeutic and other uses. It relates particularly to viscoelastic compositions that have high concentrations of highly fluorinated or perfluorinated compounds.

BACKGROUND OF THE INVENTION

Fluorocarbons have numerous biomedical applications because of their essential characteristics of high chemical and biological inertness and their capacity to dissolve a considerable amount of gases, particularly oxygen, carbon dioxide and air per unit volume. Indeed, at 37° C. under a pure oxygen atmosphere, a fluorocarbon can dissolve about a 50% volume of oxygen.

Compositions of fluorocarbons can also be used for the treatment of wounds, for example burns, as described in U.S. Pat. No. 4,366,169. According to this disclosure, the wound is put in contact with a liquid fluorocarbon directly, or indirectly through a dressing, for example a sponge, gauze, foam, dispersion or gel into which the fluorocarbon has been incorporated. However, the '169 patent does not disclose a high concentration fluorocarbon formulation or a procedure for preparing a fluorocarbon-rich gel.

High concentration fluorocarbon formulations can increase the gas-transfer capacity of preparations for topical application, improving their therapeutic effects and protecting the tissues coated therewith. Highly viscous preparations of this type can be easily applied to the wounded tissues.

Fluorocarbons have been used in the form of emulsions or water-rich gels. Known gel formulations contain low concentrations of fluorocarbons and require stabilizing or thickening agents to maintain a desirable consistency. Thus, U.S. Pat. No. 5,073,378 describes compositions for the treatment of burns, obtained from solutions of collagen, containing a growth-factor derived from platelets, and a fluorocarbon phase whose perfluorocarbon content is low. U.S. Pat. No. 4,917,930 and EP-A-0158996 describe compositions in the form of fluorocarbon emulsions comprising no more than 50% fluorocarbon by weight, or about 25% fluorocarbon by volume. These compositions are obtained by preparing an initial dispersion comprising a fluorocarbon and a surfactant complexed with the fluorocarbon, and then concentrating the fluorocarbon phase of the dispersion, for example by centrifugation, separating the fluorocarbon-rich phase, and redispersing this phase in an aqueous medium optionally containing a surfactant. Although this procedure makes it possible to limit the quantity of surfactant used, does not provide formulations having fluorocarbon concentrations greater than 50% by weight. The emulsions obtained by this process are used for injectable purposes.

U.S. Pat. No. 4,569,784 describes a stable gel of fluorocarbon also comprising no more than 50% by volume of fluorocarbon, which requires considerable quantities of surfactant for stabilization. This gel is prepared by a similar complex procedure of concentrating an emulsion by centrifugation, and requires high-pressure apparatus or the use of ultrasounds.

The document FR-A-2 630 347 describes fluorocarbon gels comprising, by contrast with those described in the above patents, a high proportion of water, about 60 to 98% by weight.

WO-A-93/09762 describes the use of fluorocarbon suspensions or emulsions for intravascular applications, containing at most 90 g/100 ml (about 50% v/v).

WO-A-90/15807 describes the use of phosphorous fluorinated surfactants in fluorocarbon emulsions and other compositions containing at most 70% in volume of fluorocarbons.

Obraztsov (poster contribution to the Vth ISBS, San Diego Calif., U.S.A., March 1993) describes an emulsion prepared from a mixture of fluorocarbons containing perfluorodecalin (80% w/v, 40% v/v), emulsified using a polyoxyethylene/polyoxypropylene copolymer (Proxanol 268) and gelified by 1,2-propyleneglycol. Preliminary studies have shown that this emulsion has a beneficial effect on the speed of cicatrization of burns and surgical wounds (activation of keratinocytes) and should be more efficacious than the biostimulating medicaments traditionally used (methyluracyl and solkoseryl). But the fluorocarbon content of these preparations does not exceed 50% by volume and the gelification is obtained by the use of a non-surfactant diol.

SUMMARY OF THE INVENTION

According to the invention there are provided compositions comprising fluorinated hydrocarbon compounds, in the form of a viscoelastic gel, comprising an oily phase containing at least one linear, branched, or cyclic fluorinated hydrocarbon compound, or derivative thereof, wherein at least about 30% of the hydrogen atoms of the compound are substituted by fluorine, the fluorinated hydrocarbon compound representing from about 75 to 99.7% (v/v) of the composition together with an aqueous phase representing from about 0.3 to 25% (v/v) of the composition and at least one surfactant chosen from the group consisting of fluorinated surfactants, alone or in a mixture with at least one hydrocarbon surfactant, the surfactant or combined surfactants representing from about 0.1 to 10% (w/v) of the composition.

In a preferred embodiment, the fluorinated hydrocarbon is perfluorinated. The perfluorinated compound is preferably selected from the group consisting of perfluoroperhydrofluoranthrene, perfluorodecalin, perfluoroperhydrophenanthrene, bis (perfluoro-hexyl)-1,2-ethene, perfluoroisopropyldecalin, a mixture of perfluorodixylylmethane and perfluorodixylylethane, and a mixture of perfluoroperhydrophenanthrene and perfluoro n-butyl decalin. In yet other preferred embodiments, the fluorinated hydrocarbon compound represents at least about 80% v/v, or at least about 90% v/v of the composition. According to other preferred embodiments of the invention, the fluorinated hydrocarbon compound comprises from 2 to 20 carbon atoms.

According to another aspect of the invention, the gel comprises at least one fluorinated hydrocarbon derivative compound wherein at least one of the heteroatoms N, O or S is inserted in the carbon chain. In a preferred embodiment of this aspect of the invention, the fluorinated hydrocarbon compound is an ether or a polyether.

According to yet another aspect of the invention, the hydrogen atoms of the fluorinated hydrocarbon compound are substituted by Br or Cl in addition to F. In preferred species of this aspect of the invention, the fluorinated hydrocarbon compound is selected from the group consisting of the halogenated fluorocarbon derivatives $C_6F_{13}Br$, $C_8F_{17}Br$, $C_6F_{13}CBr_2CH_2Br$, 1-bromo 4-perfluoro-isopropyl cyclohexane, $C_8F_{16}Br_2$, and $C_2F_3Cl_3$.

According to another aspect of the invention the gel comprises a fluorinated hydrocarbon compound selected from the group consisting of fluorocarbon compounds and their derivatives having a boiling point of 140° C. or greater.

According to preferred embodiments, the viscoelastic gels of the invention comprise perfluorodiisopropyldecalin, a mixture of perfluoroperhydrophenanthrene and perfluoro n-butyldecalin, bis(perfluorohexyl)1,2-ethene, a mixture of perfluorodixylylmethane and perfluorodixylylethane, perfluorodecalin, or perfluorooctylbromide.

According to another aspect of the invention, the composition includes a fluorinated surfactant that is an amine oxide having the formula $R_F$ $(CH_2)_n CONH—R^1N$ (O) $R^2R^3$. The surfactant is preferably pentadecafluoroheptylamido-propyldimethylamine oxide. In a particularly preferred embodiment of this aspect of the invention, at least one fluorinated surfactant is a fluorinated substituted phosphocholine, such as 2-(heptadecafluorooctyl)-ethylphosphocholine.

The surfactant can also include a fluorinated telomeric compound. In a preferred embodiment, the telomeric compound is derived from tris(hydroxymethyl)amidomethane.

Preferably the weight ratio of total surfactant to aqueous phase is from about 0.1% to 10% w/v.

The gel compositions of the invention can further comprise at least one additive substance present in either the aqueous or the oily phase or in each of the two phases.

In preferred embodiments the additive substance is a therapeutic agent selected from the group consisting of nutritive agents, medicinal substances, mineral salts, oncotic and osmotic agents, buffers, and agents that filter visible or ultraviolet light radiation.

According to yet another aspect of the invention there is provided a method for preparing a composition of one or more fluorinated hydrocarbon compounds in the form of a viscoelastic gel, comprising the steps of dispersing at least one fluorinated surfactant in an aqueous phase, in a ratio by weight of surfactant to water from about 0.1% to 10.0% w/v; and adding to the dispersion a quantity of an oily phase comprising at least one linear, branched or cyclic fluorinated hydrocarbon compound, or derivative thereof, wherein at least about 30% of the hydrogen atoms are substituted by fluorine, in an amount of at least about 75% v/v, to form a gel. In preferred embodiments, the gel is degassed and/or heat sterilized after being formed.

The invention also includes fluorocarbon gels prepared by the method of the invention, as well as medical devices comprising a gel of the invention and methods for topically treating the skin of a mammal in need thereof comprising applying to the skin a medical device according to the invention.

According to other aspects of the invention there are provided pharmaceutical or cosmetic or barrier formulations comprising a fluorocarbon gel composition according to the invention or prepared by the method of the invention.

DETAILED DESCRIPTION OF THE INVENTION

The present invention provides compositions comprising highly fluorinated or perfluorinated organic compounds formulated as gels having highly viscoelastic properties. It also provides procedures to gelify fluorocarbon. Certain of these compositions are perfectly transparent. The compositions are useful in many applications, but particularly in medicine, pharmacy, cosmetics and in biological applications.

These compositions, having a higher fluorocarbon concentration than previously known compositions of the same type, are advantageously used as topical applications. The compositions are stable, easily sterilized by heat, and are easy to prepare without requiring thickening by addition of a gelifying agent.

According to the invention, the composition of one or more fluorinated organic compounds in the form of a viscoelastic gel, stable and permeable to gases, comprises:

an oily phase comprising at least one highly fluorinated or inated organic compound, the highly fluorinated or perfluorinated organic compound(s) representing 75 to 99.7% v/v (volume/volume) of the composition;

at least one surfactant chosen from perfluoroalkylated surfactants, alone or in a mixture with one or more hydrogenated surfactants, the total surfactant representing from about 0.1 to 10% w/v (weight/volume) of the composition; and an aqueous phase representing 0.3 to 25% (v/v) of the composition.

Definitions

In the description of the invention:

gel designates a semi-solid, apparently homogenous substance which can have the consistency of gelatin.

highly fluorinated or perfluorinated compound designates linear, branched or cyclic hydrocarbons, saturated or unsaturated, or derivatives of these, which are partially or totally fluorinated.

perfluorinated designates a totally fluorinated compound.

partially fluorinated signifies that at least 30% of the hydrogen atoms of the hydrocarbon or of its derivative have been replaced by fluorine atoms.

derivatives are fluorinated hydrocarbon compounds, for example, wherein heteroatoms, such as O or S, are inserted into the carbon chain and/or wherein the hydrogen atoms of the hydrocarbon are substituted by Br, Cl or I as well as fluorine.

The fluorinated organic compound can be chosen, for example, among the fluorinated and perfluorinated hydrocarbon compounds such as linear, branched, cyclic or polycyclic perfluoroalkanes, perfluoroethers, perfluoropolyethers, perfluoroamines, freons, mixed fluorinated/ hydrogenated compounds, perfluoroalkyl bromides or chlorides and mixed derivatives, which can be partially fluorinated and partially hydrogenated. Suitable compounds are perfluorodecalin, 1,2-bis (F-alkyl) ethenes (1,2-bis (F-butyl) ethene, 1-F-isopropyl, 2-F-hexylethene and 1,2-bis (F-hexyl) ethene), perfluoromethyldecalin, perfluorodimethyldecalin, perfluoromethyl-, and dimethyladamantane, perfluoromethyl dimethyl-and trimethylbicyclo (3,3,1) nonane and homologs, perfluoroperhydrophenanthrene, ethers of formulae: $(CF_3)_2CFO$ $(CF_2CF_2)_2OCF$ $(CF_3)_2$, $(CF_3)_2CFO$ $(CF_2CF_2)_3OCF$ $(CF_3)_2$, $(CF_3)_2CFO$ $(CF_2CF_2)_2F$, $(CF_3)_2CFO$ $(CF_2CF_2)_3F$, $F[CF$ $(CF_3)$ $CF_2O]_2CHFCF_3$, $[CF_3CF_2CF_2(CF_2)_u]_2O$ with u=1, 3 or 5, amines $N(C_3F_7T)_3$, $N(C_4F_9)_3$, N $(C_5F_{11})_3$, perfluoro-N-methylperhydroquinoline and perfluoro-N-methylperhydroisoquinoline, perfluoroalkyl hydrides such as $C_6F_{13}H$, $C_8F_{17}H$, $C_8F_{16}H_2$, the halogenated derivatives $C_6F_{13}Br$, $C_8F_{17}Br$ (perflubron™, Alliance Pharmaceutical Corp., San Diego, Calif.) , $C_6F_{13}CBr_2CH_2Br$, 1-bromo 4 -perfluoro-isopropyl cyclohexane, $C_8F_{16}Br_2$, and $CF_3O(CF_2CF_2O)_uCF_2CH_2OH$ with u=2 or 3. Examples of suitable mixed fluorinated/hydrogenated compounds are $C_6F_{13}C_{10}H_{21}$, $C_6F_{13}CH=CHC_6H_{13}$, $C_8F_{17}CH=CHC_8H_{17}$. Examples of suitable fluorinated polyethers are $CF_3[(OCF_2CF_2)_p(OCF_2)_q CF_3$, where p/q=0.6 to 0.7. These compounds can be used alone or in mixtures.

According to a preferred embodiment, the highly fluorinated or perfluorinated compound used comprises from 2 to 20 carbon atoms, preferably from 6 to 20 carbon atoms and more preferably from 8 to 20 carbon atoms.

Preferably, according to the invention, the highly fluorinated or perfluorinated compound of the composition has a high boiling point, for example above 140° C., so that its evaporation is slow and it is well adapted to use in the form of a salve or ointment. For applications in which a faster evaporation of a fluorocarbon from a gel is desirable, a fluorocarbon having a lower boiling point can be used.

Examples of high boiling point fluorocarbon compounds are:

perfluoroperhydrophenanthrene (bp 215° C.)

perfluoroperhydrofluoranthrene (bp 240° C.)

perfluorotributylamine (bp: 178° C.)

bis (perfluorohexyl) 1,2-ethene (bp 195° C.)

perfluorofluorene (bp 194° C.); and APF-215™, APF-240™, APF-260™(Air Products, U.S.A.) (bp 215,216 and 260° C. respectively).

Other highly fluorinated compounds useful in the invention are perfluorodiisopropyldecal in perfluoro n-butyldecalin perfluorodixylylmethane perfluorodixylylethane perfluorooctyl bromide perfluoropolyethers, for example, the fomblins™ of Ausimont of various molecular weights, for examples MW 2500 and 3300, $C_{10}F_{21}H$ $C_2F_3Cl_3$ The surfactants used in the invention can be perfluoroalkylated surfactants alone or in mixtures with one or more hydrogenated surfactants. The surfactants can be non-ionic, anionic, cationic or zwitterionic or mixtures thereof.

For applications in the biomedical or cosmetic field, surfactants known by those skilled in the art to be the most biocompatible are used. Accordingly, perfluoroalkylated surfactants are preferred, as they are much more efficacious and less toxic than their hydrocarbon analogs, particularly because they have low hemolytic activity (J. G. Riess et al, Adv. Mat., 3:249–251 (1991).

For example, compounds of amine oximes described herein after were tolerated at doses up to 1.25 g/kg after intravenous injection in mice of a dispersion of these compounds in physiologic water. Compounds of WO-A-91/914689, telomeric amphiphilic surfactants, used in this invention are tolerated up to 4 g/kg after intravenous injection in mice of a dispersion of these compounds in physiological water.

Examples of suitable perfluoroalkylated surfactants are the amine oxides described in U.S. Pat. No. 3,828,085, in particular those having the formula (I):

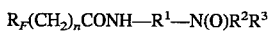

wherein $R_F$ is a perfluoroalkylated group of from 4 to 12 carbon atoms;

$R^1$ is an alkyl group of from 1 to 6 carbon atoms;

$R^2$ and $R^3$, which can be identical or different, are selected from the group consisting of alkyl groups of from 1 to 6 carbon atoms or alkyl groups of from 2 to 16 carbon atoms having a hydroxyl terminus; or fluorinated phosphorus derivatives such as those described in WO-A-90/5807, in particular fluorinated derivatives of phosphocholine, or fluorinated telomeric surfactants such as those described in WO-A-91/914689.

The quantities of surfactants used in the gels of the invention are preferably low (0.1 to 10% w/v) and are chosen in relation with the quantity of aqueous phase used such that the weight ratio of surfactant/aqueous phase is from 1/10 to 1, preferably from 1/5 to 1/3.

The compositions of the invention can be prepared by low-energy mechanical homogenization techniques, in particular, which are far easier to operate than those such as sonication or high-energy homogenization formerly used for the preparation of fluorocarbon gels.

Thus, the invention provides a procedure for the preparation of the composition of fluorinated organic compounds described above, comprising the steps of:

(a) dispersing at least one suitable surfactant in the aqueous phase, for example by mechanical stirring;

(b) progressively adding to the dispersion of step (a), under stirring, the required quantity of oily phase fluorocarbon to form a gel of fluorinated compound(s); and optionally (c) degassing the gel of step (b).

The degassing can be done, for example, by centrifugation at room temperature.

Using the procedure described, a concentrated gel is obtained without the necessity of an intermediate step of preparing an emulsion which is then concentrated by centrifugation by expensive techniques or thickened as described in the prior art. The preparation of gels is far simpler than that described in U.S. Pat. No. 4,569,784 for preparing fluorocarbon emulsions because the techniques of low-energy dispersion are sufficient to form the gels, whereas for the preparation of classical emulsions, mechanical high-pressure homogenizers of the Manton-Gaulin type, or microfluidizer or ultrasound must be used.

When the composition of the invention is to be used for biomedical applications, the gel can be sterilized; this can be done, for example, by heating in a static autoclave under standard procedures.

When the composition comprises additives, these can be added to the aqueous phase, the oily phase or to both phases. The additives can be mineral salts, buffers, oncotic and osmotic agents, nutritive agents, active principles, medicinal substances, filters of particular rays, or other ingredients that improve the stability, efficacy and biological tolerance of the compositions.

The compositions of fluorinated compounds of the invention present characteristics very different from those of known emulsions and fluorocarbon gels. The fluorocarbon compositions of the invention are often in the form of transparent gels, as compared to the milky emulsions of known fluorocarbon compositions. Also, the concentration of perfluorinated compound of the present gel compositions is far higher (75 to 99.7% v/v) than the maximum concentration of up to about 70% (v/v) in known compositions, and the ratio of surfactant to the highly fluorinated or perfluorinated compounds, necessary for the preparation of the composition, is far lower than that used in known compositions.

The quantity of water which can be incorporated in the gel is variable and can be adapted to the intended application. Indeed, some compositions may contain only 0.3% of water, but others may contain up to 25% (v/v) of water. In the latter case, greater quantities of surfactant are generally used, because for a given concentration of surfactant, the viscosity of the gel is decreased as the quantity of water increases. For a given amount of water, the viscosity can be increased by increasing the proportion of surfactant. A surfactant to aqueous phase ratio of 1/5 generally provides a satisfactory viscosity for many uses.

Moreover, the preparation of the gels of the invention does not require the addition of a gelifying agent, and these gels can be sterilized by heat under standard conditions, and stored for several months at room temperature, without apparent degradation.

The compositions of highly fluorinated or perfluorinated compounds of the invention can find numerous applications, in particular in cosmetics and pharmacy as well as in light radiation protective sunscreens or other barrier creams. Their use in ophthalmology is also contemplated. They can also be used in cutaneous applications for the healing of wounds, burns, and bruises, and for the reduction of hypertrophic scars. Indeed, highly fluorinated or perfluorinated compounds, being both hydrophobic and lipophobic, have the property, when spread over the skin (the wound), of isolating the skin and forming a barrier to all forms of contamination and to dust, while remaining permeable to gas and particularly to oxygen. An efficacious protection can also be obtained with thin films of gel of highly fluorinated or perfluorinated compounds. Moreover, these gels can also contain medicaments, for example growth-factors, antibiotics, nutritive elements or other beneficial substances, for example hydrating agents, which will thus be delivered at the appropriate site. The gels of highly fluorinated or perfluorinated compounds have in addition lubricating properties, improving slipperiness and reducing friction.

The compositions of the invention can also be used to realize more complex formulations permitting the simultaneous delivery of hydrophilic and lipophilic drugs.

The compositions of the invention can also be incorporated into a dressing to be applied on the skin. The term dressing here includes any medical material destined to maintain the gel in contact with the skin and perhaps to apply pressure, for topical treatments in the biomedical or cosmetic field. The gels can be incorporated into or deposited on various supports for other applications.

The compositions of the invention can also be used in any application related to the particular properties of the compositions and in particular to their highly viscoelastic character, their transparency, their surface active character, their chemical inertness, their permeability to oxygen, and if necessary to those of other additives present in the composition.

Other characteristics and advantages of the invention will be more clearly seen on reading the following examples, which are illustrative, not limitative.

The present invention is described in detail using the following examples; however, the methods described therein are broadly applicable, and are not to be understood as limited thereby in any way whatsoever. In the following examples, all temperatures are set forth uncorrected in degrees Celsius.

EXAMPLES

Examples 1 to 7

Preparation of perfluorodiisopropyldecalin gel (APF-240)™.

In these examples, pentadecafluoroheptylamidopropyldimethylamine oxide (F7AO) is used as a surfactant. The appearance of the gels obtained in Examples 1–7 was unchanged after 1 year of storage at room temperature.

Example 1

In this example, a high proportion of fluorocarbon (99% v/v) was used. The surfactant F7AO (0.045 g) was dispersed by mechanical stirring in water for injectable preparations (0.225g) at a temperature of 20° to 30° C. A quantity of 22.28 ml of perfluorodiisopropyldecalin (44.55 g) was then added under a flow of nitrogen at 20°–30° C., while stirring with a mixer, and the stirring was continued for 10 min. A gel containing 99.0% v/v fluorocarbon, 1.0% v/v of water, and 0.2% w/v of surfactant was obtained.

The gel thus obtained was degassed by centrifugation at 1000 rpm for 15 min at room temperature, then conditioned in 5 ml flasks and sterilized in a static autoclave at 121° C. for 15 min under a pressure of $10^5$Pa ($10^5$N/m$^2$). The viscosity of the gel at 25° C. was determined with a Bohlin CS rheometer (3 ml cells). The composition and viscosity of the gels are shown in Table I.

Example 2

The procedure described in Example 1 was followed to prepare a fluorocarbon gel composition, using 0.112 g of surfactant F7AO, 0.562 g of injectable water and 21.94 ml (43.88 g) of perfluorodiisopropyldecalin. A gel containing 97.5% v/v of fluorocarbon, 2.5% v/v of water and 0.5% w/v of surfactant was thus obtained.

Example 3

The procedure described in Example 1 was followed starting with 0.225 g of surfactant F7AO, 1.125 g of injectable water and 21.37 ml (42.75 g) of perfluorodiisopropyldecalin.

Example 4

The procedure described in Example 1 was followed to prepare a gel using 0.187 g of surfactant F7AO, 0.560 g of injectable water and 21.94 ml (43.88 g) of perfluorodiisopropyldecalin.

Example 5

The procedure described in Example 1 was followed starting with 0.750 g (3.33% w/v) of F7AO, 2.25 g (10% v/v) of injectable water and 20.25 ml (40.50 g, 90% v/v) of perfluorodiisopropyldecalin.

Example 6

The procedure described in Example 1 was followed starting with 0.9 g (4% w/v) of F7AO, 4.5 g (20% w/v) of injectable water and 18.00 ml (80% v/v) of perfluorodiisopropyldecalin.

Example 7

The procedure described in Example 1 was followed starting with 0.023 g of F7AO (0.1% w/v), 0.12 g of injectable water (0.5% v/v), and 22.3 ml (99.5% v/v) of perfluorodiisopropyldecalin.

Example 8

Preparation of a gel of perfluoroperhydrophenanthrene and perfluoro n-butyldecalin (APF-215)™.

A gel of perfluoroperhydrophenanthrene and perfluoro n-butyldecalin at a combined concentration of 99% in volume was prepared following the procedure described in Example 1 but using the following components:

Perfluoroperhydrophenanthrene and perfluoro n-butyldecalin: 22.27 ml (44.55 g) injectable water: 0.225 g (1% v/v) surfactant F7AO: 0.045 g (0.2 % w/v).

No modification in the appearance of the gel was seen after one year of storage at room temperature.

Example 9

A low viscosity gel of perfluoroperhydrophenanthrene and perfluoro n-butyldecalin at a combined concentration of 90% in volume was prepared following the procedure described in Example 1 but using the following components:

| | |
|---|---|
| perfluoroperhydrophenanthrene and n-butyldecalin | 9 ml |
| injectable water | 1 ml (1% w/v) |
| $C_8F_{17}(CH_2)-S-(CH_2-CH)_5-H$<br>　　　　　　　　　　｜<br>　　　　　　　　　　$C=O$<br>　　　　　　　　　　｜<br>　　　　　　　　　　$NH-CH(CH_2OH)_3$ | 0.2 g (2% w/v) |

Example 10

Preparation of a gel of bis(perfluorohexyl)1,2-ethene.

The procedure described in Example 1 was followed to prepare a concentrated gel (99% in volume) of bis (perfluorohexyl) 1,2 -ethene, using the following components:

bis (F-hexyl) 1,2-ethene: 22.27ml; injectable water: 0.225 g (1% v/v); and surfactant F7AO: 0.045 g (0.2% w/v)

No change in the appearance of the gel obtained in was seen after one year of storage at room temperature.

Examples 11 to 13:

Preparation of gels of various fluorocarbons concentrated to 95% in volume, using F7AO as surfactant.

In these examples, various fluorocarbons, and the same proportions of fluorocarbon (95% v/v), water (5% v/v) and surfactant (1% w/v) are used.

Example 11

The procedure described in Example 1 was followed to prepare a fluorocarbon gel, but using as fluorocarbon APF-260™, i.e. a mixture of perfluorodixylylmethane and perfluorodixylylethane.

The quantities of fluorocarbon, water and fluorinated surfactant were as follows:

fluorocarbon APF-260™: 21.37 ml (42.75 g) injectable water: 1.125 g, and surfactant F7AO: 0.225 g.

Example 12

The procedure of Example 1 was used. In addition the mixed fluorocarbon/hydrocarbon surfactant compound $C_6F_{13}C_{10}H_{21}$ was dispersed with F7AO in water.

Fluorocarbon APF-260: 94% V/v $C_6F_{13}C_{10}H_{21}$: 0.74% v/v

F7AO : 0.82% w/v

Injectable Water 5.26% w/V

The gel is stable for at least one year.

Example 13

The procedure described in Example 1 was followed to prepare a gel of perfluorodecalin, using the following components:

perfluorodecalin: 21.37 ml, 41.46, g injectable water: 1.125 g, and surfactant F7AO: 0.225 g.

Example 14

A gel of perfluorooctyl bromide was prepared, following the same operation procedure as in Example 1, but using the following components:

perfluorooctyl bromide: 21.37 ml, 41.03g, injectable water: 1.125 g, and surfactant F7AO: 0.225 g.

Example 15

Preparation of a gel of perfluorooctyl bromide using as surfactant 2-(heptadecafluorooctyl)ethylphosphocholine (F8C2PC)

The procedure described in Example 1 was followed to prepare this perfluorooctyl bromide gel, using the following components:

perfluorooctyl bromide: 21.37 ml, 41.03 g (95% v/v)

injectable water: 1.125 g (5% v/v), and surfactant F8C2PC: 0.225 g (1% w/v).

Examples 16 to 19:

Preparation of gels of perfluoropolyethers of different molecular weights concentrated to 99 and 95% by volume, using F7AO as surfactant.

Example 16

Perfluoropolyether (Ausimont, (I-20121 Milan, Italy) Product, MW(aver)=2500 (99% v/v)

The procedure described in Example 1 is followed to prepare a gel of perfluoropolyether concentrated to 99% by volume, using the following components:

perfluoropolyether: 22.27 ml injectable water: 0.225 g (1% v/v)

surfactant F7AO: 0.045 g (0.2% w/v)

The appearance of the gel obtained was unchanged after months storage at room temperature.

Example 17

Perfluoropolyether (Ausimont Product, $MW_{av}$=2500 g (95% v/v)

The procedure described in Example 1 is followed to prepare a gel of perfluoropolyether concentrated to 95% by volume, using the following components:

perfluoropolyether: 21.37 ml injectable water: 1.125 g (5% v/v)

surfactant F7AO: 0.225 g (1% w/v)

The appearance of the gel remained unchanged after 3 months storage at room temperature.

Example 18

Perfluoropolyether (Ausimont Product, MW=3300 g) (99% v/v)

The procedure described in Example 1 is followed, to prepare a gel of perfluoropolyether concentrated to 99% by volume, using the following components:

perfluoropolyether: 22.27 ml injectable water: 0.225 g (1% v/v)

surfactant F7AO: 0.045 g (0.2% w/v)

The appearance of the gel obtained was unchanged after months storage at room temperature.

Example 19

Perfluoropolyether (Ausimont) $MW_{av}$=3300 g) (95% v/v)

The procedure described in Example 1 was followed to prepare a gel of perfluoropolyether concentrated to 95% by volume, using the following components:

perfluoropolyether: 21.37 ml injectable water: 1.125 g (5% v/v)

surfactant F7AO: 0.225 g (1% w/v)

The appearance of the gel obtained was unchanged after 3 months storage at room temperature.

Example 20

Preparation of a gel of $C_2F_3Cl_3$ at 99% by volume using F7AO as surfactant.

The procedure described in Example 1 was followed to prepare a gel of $C_2F_3Cl_3$ concentrated at 99% by volume, using the following components:

| | | |
|---|---|---|
| $C_2F_3Cl_3$: | 6.33 ml | (99% v/v) |
| Injectable Water: | 0.1 ml | (1% v/v) |
| Surfactant F7AO: | 0.02 g | (0.2% w/v) |

Examples 21–22

Tolerance of the concentrated fluorocarbon gel

Example 21

The gel formulation of Example 7 was tested for adverse effects on normal and scarified skin of 3 rabbits, as follows.

A quantity of 0.5 ml of the gel was applied to the skin of the animals for 4 hours with a semi-obstructed dressing. The dressing was then removed and the reactions were noted after 1 hour and every day for 14 days. No irritation was observed on the normal and the scarified skin.

Example 22

The procedure of Example 21 was followed using the gel of Example 7 (fluorocarbon 95% v/v, F7AO 1% w/v, water 5% v/v). No irritation was observed after 14 days.

TABLE I

| Examples | Fluorocarbon (% v/v) | Water (% v/v) | Surfactants (% w/w) | Ratio of Surfactant/ Water | Viscosity (Pa · s) at $0.1s^{-1}$ |
|---|---|---|---|---|---|
| 1 | perfluorodiiso-propyldecalin (99) | 1 | F7AO 0.2 | 1/5 | 140.2 |
| 2 | perfluorodiiso-propyldecalin (97,5) | 2.5 | F7AO 0.5 | 1/5 | 83.2 |
| 3 | perfluorodiiso-propyldecalin (95) | 5 | F7AO 1 | 1/5 | 56.5 |
| 4 | perfluorodiiso-propyldecalin (97,5) | 2.5 | F7AO 0.83 | 1/3 | 203.5 |
| 5 | perfluorodiiso-propyldecalin (90) | 10 | F7AO 3.33 | 1/3 | 122.7 |
| 6 | perfluorodiiso-propyldecalin (80) | 20 | F7AO 4 | 1/5 | 57.9 |
| 7 | perfluorodiisopropyl decalin (99.5) | 0.5 | 0.1 | 1/5 | — |
| 8 | perfluoroperhydro phenanthrene and perfluoro n-butyldecalin (99) | 1 | F7AO 0.2 | 1/5 | 64.07 |
| 10 | Bis(perfluorohexyl) 1,2-ethene (99) | 1 | F7AO 0.2 | 1/5 | — |
| 11 | Perluorodixylyl methane and perfluorodixylyl ethane (95) | 5 | F7AO 1 | 1/5 | — |
| 13 | Perfluorodecalin (95) | 5 | F7AO 1 | 1/5 | — |
| 14 | Perfluorooctyl bromide (95) | 5 | F7AO 1 | 1/5 | — |
| 15 | Perfluoroocytl bromide (95) | 5 | F8C2PC 1 | 1/5 | — |

The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

What is claimed is:

1. A composition comprising fluorinated organic compounds, in the form of a viscoelastic gel, comprising:

an oily phase comprising at least one linear, branched, or cyclic fluorinated hydrocarbon compound, or derivative thereof, wherein at least about 30% of the hydrogen atoms of the compound are substituted by fluorine, the fluorinated hydrocarbon compound representing from about 75 to 99.7% (v/v) of the composition;

an aqueous phase representing from about 0.3 to 25% (v/v) of the composition;

at least one surfactant chosen from the group consisting of fluorinated surfactants, alone or in a mixture with at least one hydrocarbon surfactant, the surfactant or combined surfactants representing from about 0.1 to 10% (w/v) of the composition.

2. A composition according to claim 1, wherein the fluorinated hydrocarbon is perfluorinated.

3. A composition according to claim 1, wherein the fluorinated hydrocarbon compound represents at least about 80% v/v of the composition.

4. A composition according to claim 1, wherein the fluorinated hydrocarbon compound represents at least about 90% v/v of the composition.

5. A composition according to claim 1 wherein the fluorinted hydrocarbon compound comprises from 2 to 20 carbon atoms.

6. A composition according to claim 1 comprising a fluorinated hydrocarbon derivative compound wherein at least one of the heteroatoms N, O or S in inserted in the carbon chain.

7. A composition according to claim 6 wherein the fluorinated hydrocarbon compound is an ether or a polyether.

8. A composition according to claim 1 wherein the hydrogen atoms of said fluorinated hydrocarbon compound are substituted by Br or Cl in addition to F.

9. A composition according to claim 8 wherein the fluorinated hydrocarbon compound is selected from the group consisting of the halogenated fluorocarbon derivatives $C_6F_{13}Br$, $C_8F_{17}Br$, $C_6F_{13}CBr_2CH_2Br$, 1-bromo 4-perfluoroisopropyl cyclohexane, $C_8F_{16}Br_2$, and $C_2F_3Cl_3$.

10. A composition according to claim 2, wherein the perfluorinated compound is selected from the group consisting of perfluoroperhydrofluoranthrene, perfluorodecalin, perfluoroperhydrophenanthrene, bis(perfluoro-hexyl)-1,2-ethene, perfluoroisopropyldecalin, a mixture of perfluorodixylylmethane and perfluorodixylylethane, and a mixture of perfluoroperhydrophenanthrene and perfluoro n-butyl decalin.

11. A composition according to claim 1 wherein the fluorinated hydrocarbon compound is selected from the group consisting of fluorocarbon compounds and their derivatives having a boiling point of 140° C. or greater.

12. A composition according to claim 1 wherein the fluorinated surfactant is an amine oxide having the formula $R_F(CH_2)_nCONH—R^1N(O)R^2R^3$ wherein $R_f$ is a perfluoroalkyl group having from 4 to 12 carbon atoms;

$R^1$ is an alkyl group having from 1 to 6 carbon atoms;

$R^2$ and $R^3$, which can be identical or different, are selected from the group consisting of alkyl groups having from 1 to 6 carbon atoms and alkyl groups having from 2 to 16 carbon atoms and having terminal hydroxyl groups; and n=0 to 12.

13. A composition according to claim 12 wherein the surfactant is pentadecafluoroheptylamidopropyldimethylamine oxide.

14. A composition according to claim 1 wherein at least one fluorinated surfactant is a fluorinated substituted phosphocholine.

15. A composition according to claim 14 wherein the surfactant is 2-(heptadecafluorooctyl)ethylphosphocholine.

16. A composition according to claim 1 wherein the surfactant includes a fluorinated telomeric compound.

17. A composition according to claim 16 wherein the surfactant includes a telomeric compound derived from tris(hydroxymethyl)amidomethane.

18. A composition according to claim 1 comprising perfluorodiisopropyldecalin.

19. The composition of claim 1 comprising a mixture of perfluoroperhydrophenanthrene and perfluoro n-butyldecalin.

20. The composition of claim 1 comprising bis(perfluorohexyl)1,2-ethene.

21. The composition of claim 1 comprising a mixture of perfluorodixylylmethane and perfluorodixylylethane.

22. The composition of claim 1 comprising perfluorodecalin.

23. The composition of claim 1 comprising perfluorooctylbromide.

24. The compositions of any of claims 18–23 comprising the surfactant pentadecafluoroheptylamidopropyldimethylamine oxide.

25. A composition according to claim 1 wherein the weight ratio of total surfactant to aqueous phase is from about 1/10 to 1/1.

26. A composition according to claim 1 wherein the weight ratio of total surfactant to aqueous phase is from about 1/5 to 1/3.

27. A composition according to claim 1 further comprising at least one additive substance present in either the aqueous or the oily phase or in each of the two phases.

28. A composition according to claim 27, wherein the additive substance is a therapeutic agent selected from the group consisting of nutritive agents, medicinal substances, mineral salts, oncotic and osmotic agents, buffers, and agents that filter visible or ultraviolet light radiation.

29. A method for preparing a composition of one or more fluorinated hydrocarbon compounds in the form of a viscoelastic gel, comprising the steps of:

(a) dispersing at least one fluorinated surfactant in an aqueous phase, in a ratio by weight of surfactant to water of from about 0.1% to 10.0% w/v; and (b) adding to the dispersion of step (a) a quantity of an oily phase comprising at least one linear, branched or cyclic fluorinated hydrocarbon compound, or derivative thereof, wherein at least about 30% of the hydrogen atoms are substituted by fluorine, in an amount of at least about 75% v/v, to form a gel.

30. A method according to claim 29 further comprising the step of degassing the gel of step (b).

31. A method according to claim 29 or 30 further comprising the step of heat sterilization of the gel of step (b).

32. A method according to claim 29 wherein the fluorinated hydrocarbon compound is perfluorinated.

33. A method according to claim 29 wherein the fluorinated hydrocarbon is a derivative compound wherein at least one of the heteroatoms N, O or S is inserted in the carbon chain.

34. A method according to claim 33 wherein the fluorinated hydrocarbon compound is an ether or a polyether.

35. A method according to claim 29 wherein the hydrogen atoms of said fluorinated hydrocarbon compound are substituted by Br or Cl in addition to F.

36. A method according to claim 29 wherein the amount of said fluorinated hydrocarbon compound is at least about 90% v/v of the gel.

37. A method according to claim 29 wherein the fluorinated hydrocarbon compound is selected from the group consisting of the halogenated derivatives $C_6F_{13}Br$, $C_8F_{17}Br$, $C_6F_{13}CBr_2CH_2Br$, 1-bromo 4-perfluoro-isopropyl cyclohexane, $C_8F_{16}Br_2$ and $C_2F_3Cl_3$.

38. A method according to claim 29 wherein the fluorinated hydrocarbon compound is selected from the group consisting of perfluoroperhydrofluoranthrene, perfluorodecalin, perfluoroperhydrophenanthrene, bis(perfluorohexyl)1,2-ethene, perfluoroisopropyldecalin, a mixture of perfluorodixylylmethane and perfluorodixylylethane, and a mixture of perfluoroperhydrophenanthrene and perfluoro n-butyl decalin.

39. A fluorocarbon gel prepared by a method according to claim 29.

40. A method according to claim 29 wherein the surfactant is an amine oxide.

41. A method according to claim 29 wherein the surfactant is pentadecafluoroheptylamidopropyldimethylamine oxide.

42. A method according to claim 29 wherein the surfactant is a fluorinated phosphocholine.

43. A medical device comprising a composition according to claim 1 or 40.

44. A pharmaceutical or cosmetic or barrier formulation comprising a fluorocarbon composition according to claim 1 or 40.

45. A method for topically treating the skin of a mammal in need thereof comprising applying to the skin a medical device according to claim 43.

* * * * *